US010392590B1

(12) United States Patent
Jakel et al.

(10) Patent No.: US 10,392,590 B1
(45) Date of Patent: Aug. 27, 2019

(54) METHOD AND SYSTEM FOR DISTILLING ALCOHOL IN AN ALCOHOL PRODUCTION PROCESS

(71) Applicant: Fluid Quip Process Technologies, LLC, Springfield, OH (US)

(72) Inventors: Neal Jakel, Cedar Rapids, IA (US); John Kwik, Bellbrook, OH (US); Michael Hora, Marion, IA (US)

(73) Assignee: Fluid Quip Process Technologies, LLC, Springfield, OH (US)

( * ) Notice: Subject to any disclaimer, the term of this patent is extended or adjusted under 35 U.S.C. 154(b) by 0 days.

(21) Appl. No.: 16/241,081

(22) Filed: Jan. 7, 2019

(51) Int. Cl.
*C07C 31/08* (2006.01)
*C07C 29/80* (2006.01)
*B01D 3/00* (2006.01)
*B01D 5/00* (2006.01)
*C12F 3/00* (2006.01)
*C12F 3/08* (2006.01)
*B01D 3/14* (2006.01)

(52) U.S. Cl.
CPC ............... *C12F 3/08* (2013.01); *B01D 3/143* (2013.01); *B01D 5/006* (2013.01); *C07C 29/80* (2013.01); *B01D 2257/80* (2013.01); *C07C 31/08* (2013.01)

(58) Field of Classification Search
CPC .......... C07C 29/80; C07C 31/08; C12F 3/08; B01D 3/143; B01D 5/006
See application file for complete search history.

(56) References Cited

U.S. PATENT DOCUMENTS

| 2,796,120 | A  | 6/1957  | Lockman         |
| 4,305,790 | A  | 12/1981 | Kramer, Sr.     |
| 4,309,254 | A  | 1/1982  | Dahlstrom et al.|
| 4,328,074 | A  | 5/1982  | Standiford      |
| 4,358,536 | A  | 11/1982 | Thorsson et al. |
| 6,365,006 | B1 | 4/2002  | Aristovich et al.|
| 7,297,236 | B1 | 11/2007 | Vander Griend   |
| 7,572,353 | B1 | 8/2009  | Vander Griend   |
| 8,778,433 | B2 | 7/2014  | Lee             |
| 8,906,204 | B2 | 12/2014 | Xu              |
| 2007/0000769 | A1 | 1/2007 | Brown          |
| 2011/0108409 | A1 | 5/2011 | Brown          |
| 2011/0315541 | A1 | 12/2011| Xu             |

FOREIGN PATENT DOCUMENTS

| BR | 7805444 A  | 4/1979  |
| BR | 8007749 A  | 5/1981  |
| BR | 8601034 A  | 10/1987 |
| DE | 2632910 A1 | 1/1978  |

OTHER PUBLICATIONS

U.S. Patent and Trademark Office, Non-final Office Action issued in corresponding U.S. Appl. No. 15/805,520 dated Feb. 1, 2018, 29 pages.
U.S. Patent and Trademark Office, Notice of Allowance issued in corresponding U.S. Appl. No. 15/805,520 dated Jul. 6, 2018, 15 pages.
Multi-Effect Evaporators in Handbook of Evaporation Technology, pp. 166-171, William Andrew Publishing/Noyes.
Grethlein, H. E. et al. "The cost of Ethanol Production from Lignocellulosic Biomass—A Comparison of Selected Alternative Processes," Final Report, Michigan Biotechnology Institute, pp. 3-17 (1993).
Collura, Michael A. et al. "Energy-Saving Distillation Designs in Ethanol Production" Ind. Eng. Chem. Res., (1988) 27, pp. 1686-1696.
"Fuel from Farms: A Guide to Small-Scale Ethanol Production: Second Edition." pp. 43-44, (1982).
"Energy Conservation in Ethanol Production from Renewable Resources and Non-Ptroleum Energy Sources," by Center Corporation (Reston, Virigina), pp. 3-36, (1981).
May, S.C. et al. "Ethanol Production for Automotive Fuel Usage" Engineering & Economic Studies for Direct Application of Geothermal Energy, pp. 3-13, Quarterly Report, (1979).
Perlman, David et al. "Fermentation" Industrial and Engineering Chemistry, (1953) vol. 45 No. 9 pp. 1944-1969.
"Distilled Water for Boiler-Feed," Power (Dec. 27, 1921) vol. 54, pp. 998-1003, abstract only.
McAloon, Andrew et al. "Determining the Cost of Producing Ethanol from Corn Starch and Lignocellulosic Feedstocks," Technical Report, National Renewable Energy Laboratory, Oct. 2000.
Westphalen, Denis Libert, Modelagem, Simulacao e Optimizacao De Sistemas De Evaporacao, Universidade Estadual De Campinas Faculdade De Engenharia Química, Janeiro, 1999.
Grethlein, H. E. et al. "The cost of Ethanol Production from Lignocellulosic Biomass—A Comparison of Selected Alternative Processes. Final Report", pp. 3-17 (1993).
"Energy Conservation in Ethanol Production from Renewable Resources and Non-Ptroleum Energy Sources." pp. 3-36, (1981).
May, S.C. et al. "Ethanol Production for Automotive Fuel Usage" Engineering & Economic Studies for Direct Application of Geothermal Energy, pp. 3-13, (1979).
"Distilled Water for Boiler-Feed," Power (Dec. 27, 1921) vol. 54, pp. 998-1003.

(Continued)

*Primary Examiner* — Sikarl A Witherspoon
(74) *Attorney, Agent, or Firm* — Wood Herron & Evans LLP

(57) ABSTRACT

A method and system for distilling alcohol in an alcohol production process is disclosed. The method can include fermenting a mixture of water and milled grain to produce alcohol-laden beer, which can be distilled in a beer column maintained at a subatmospheric pressure to produce a vapor, primarily including alcohol, and whole stillage. Stillage is separated from the whole stillage. Water is evaporated from the separated stillage to produce first-concentrated stillage and first effect steam. Water from the first-concentrated stillage is evaporated with heat from the first effect steam to produce second effect steam. In one embodiment, second effect steam can be used to supply sufficient heat to a side stripper for distilling the alcohol-laden beer. In another embodiment, the method can include generating steam from one or more steam generator to supply sufficient heat to the beer column for distilling the alcohol-laden beer.

29 Claims, 5 Drawing Sheets

(56) References Cited

OTHER PUBLICATIONS

McAloon, Andrew et al. "Determining the Cost of Producing Ethanol from Corn Starch and Lignocellulosic Feedstocks," Oct. 2000.
Westphalen, Denis Libert, "Universidade Estadual De Campinas Faculdade De Engenharia Química," Janeiro, 1999.

METHOD AND SYSTEM FOR DISTILLING ALCOHOL IN AN ALCOHOL PRODUCTION PROCESS

TECHNICAL FIELD

The present invention relates generally to alcohol production, and more specifically, to a method and system for producing alcohol (e.g., ethanol) and/or other biofuels/biochemicals.

BACKGROUND

Fuel grade alcohol (e.g., ethanol) distilled from grain (e.g., corn) has become increasingly popular as an alternative to gasoline. Additionally, ethanol has increased in popularity as a gasoline additive for formulating clean burning grades of gasoline for motor vehicles.

One method of producing ethanol includes using a corn dry-milling process. A typical corn dry-milling process consists of four major steps: grain handling and milling, liquefaction and saccharification, fermentation and distillation, and co-product recovery. Grain handling and milling is the step in which the corn is brought into the plant and ground to promote better starch to glucose conversion. Liquefaction is the step of converting solids, such as starch, to a flowable liquid producing oligosaccharides and saccharification is where the oligosaccharides are converted into single glucose molecules. Fermentation and distillation is the process of yeast or bacteria, or clostridia, for example, converting glucose into a biofuel or a biochemical, such as ethanol. Co-product recovery is the step in which the corn by-products are de-watered and made ready. There are many known chemical and biological conversion processes known in the art that utilize yeast, bacteria, or the like to convert glucose to other biofuels and biochemical components like ethanol, for example.

The recovery of alcohol, e.g., butanol, ethanol, etc., and natural co-products generally begins with the beer (spent fermentation broth) being sent to a distillation system. With distillation, ethanol is typically separated from the rest of the beer through a set of stepwise vaporizations and condensations. To produce fuel grade ethanol, more than one interconnected distillation column is typically used to progressively purify the ethanol product. In a typical ethanol distillation process, a beer column receives beer and produces an intermediate ethanol vapor. A rectifier column receives the intermediate ethanol vapor from the beer column and produces 190 proof or 95% pure ethanol vapor. A third, side stripper column receives bottoms from the rectifier column and then produces an intermediate ethanol overhead vapor that is further purified by the rectifier column. The ethanol free bottoms from the side stripper column can be used to formulate cook water for the liquefaction portion of the process. Because of the physical properties of an ethanol water solution, a distillation process can only practically produce an ethanol water solution that is approximately 95% ethanol and 5% water. A dehydrator is used to remove most of the remaining water to produce higher purity product. The dehydrator receives the 95% ethanol vapor and removes nearly all of the remaining water to produce ethanol having a water content typically of less than about 1.0%. A dehydrator may contain beads of material that attract or retain water molecules to a greater degree than ethanol molecules or use a media to separate water and ethanol based on molecule size.

A fuel grade ethanol distillation process like the one described above also produces co-products. To that end, the beer less the alcohol extracted through distillation is known as whole stillage, which contains a slurry of the spent grains including corn protein, fiber, oil, minerals, and sugars as well as spent fermentation agent. These byproducts are too diluted to be of much value at this point and are further processed to provide the dried distiller's grains with solubles (DDGS).

In typical processing, when the whole stillage leaves the distillation column, it is generally subjected to a decanter centrifuge to separate insoluble solids or "wet cake", which includes mostly fiber, from the liquid or "thin stillage", which includes, e.g., protein, fine fiber, oil, and amino acids. After separation, the thin stillage moves to stillage evaporators to boil away moisture, leaving a thick syrup that contains soluble (dissolved) solids. The concentrated syrup can be mixed with the wet cake, and the mixture may be sold to beef and dairy feedlots as distillers wet grain with solubles (DWGS). Alternatively, the wet cake and concentrated syrup mixture may be dried in a drying process and sold as distillers dried grain with solubles (DDGS). The resulting DDGS generally has a crude protein content of about 32% and is a useful feed for cattle, other ruminants, and monogastric animals due to its protein and fiber content. The resulting product is a natural product.

A typical ethanol production process requires significant energy input as well as a significant amount of process water. It would be beneficial to provide a method and system for producing ethanol that conserves energy and water while utilizing waste heat from the evaporators to heat other portions of the process.

SUMMARY

The present invention relates to producing alcohol (e.g., ethanol) and/or other biofuels/biochemicals and, more specifically, to a method and system for distilling alcohol in an alcohol production process.

In one embodiment, a method for distilling alcohol in an alcohol production process is provided that includes fermenting a mixture of water and milled grain to produce alcohol-laden beer, then distilling the alcohol-laden beer in a beer column maintained at a subatmospheric pressure to produce a vapor, primarily including alcohol, and whole stillage, which includes stillage. Next, water is evaporated from all or a portion of the stillage via one or more evaporators and steam is generated from a fluid via one or more steam generators, which do not receive the stillage. Then, at least a portion of the generated steam from the one or more steam generators is used to supply sufficient heat to the beer column for distilling the alcohol-laden beer to produce alcohol.

In another embodiment, a system for distilling alcohol in an alcohol production process is provided that includes a beer column that receives alcohol-laden beer, the beer column distills the alcohol-laden beer at a subatmospheric pressure to produce a vapor, primarily including alcohol, and whole stillage, which includes stillage. The system further has a first effect evaporator system that includes one or more evaporators that receive all or a portion of the stillage, the one or more evaporators configured to evaporate water from the stillage. One or more steam generators also are provided that receive a fluid and are configured to generate steam from the fluid, the one or more steam generators do not receive the stillage. The beer column receives at least a portion of the generated steam from the one or more steam generators, whereby the steam provides sufficient heat for distilling the alcohol-laden beer in the beer column to produce alcohol.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

The present invention relates to producing alcohol and/or other biofuels/biochemicals and, more specifically, to a method and system for distilling alcohol (e.g., ethanol) using a grain (e.g., corn) dry-milling process.

Figure 1:
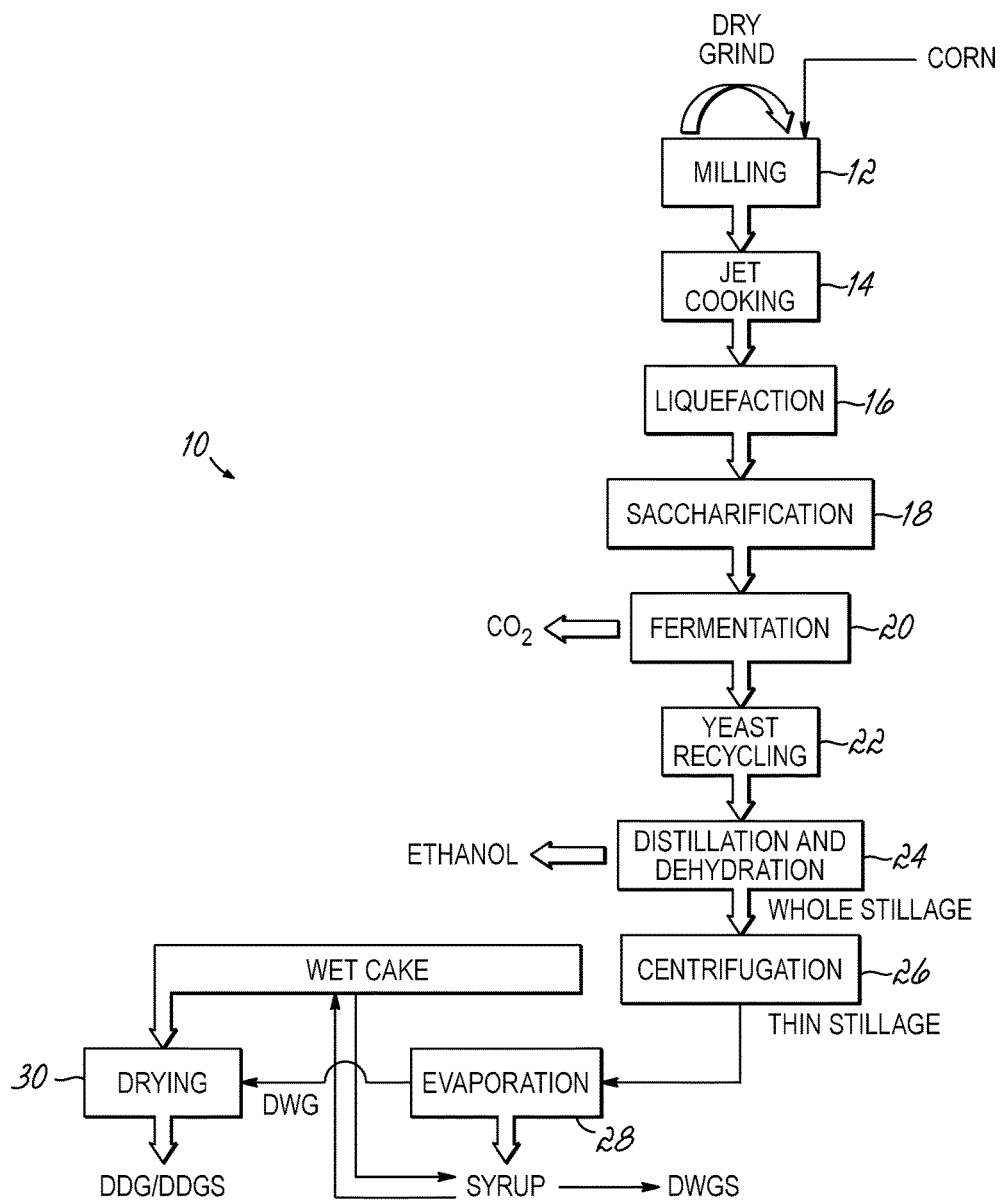
FIG. 1 is a flow diagram of a prior art dry-milling process and system for producing ethanol and distiller's grains with solubles.

FIG. 1 is a flow diagram of a prior art corn dry-milling process for producing alcohol, such process is fully discussed in U.S. Pat. No. 8,778,433, entitled "Methods for producing a high protein corn meal from a whole stillage byproduct", which is expressly incorporated by reference herein in its entirety. A significant portion of alcohol, e.g., ethanol, in the United States is produced from dry-milling processes, which convert corn into two products, namely ethanol and distiller's grains with solubles. Although virtually any type and quality of grain, such as but not limited to sorghum, wheat, triticale, barley, rye, tapioca, cassava, potato, and other starch containing grains can be used to produce ethanol, the feedstock for this process is typically corn referred to as "No. 2 Yellow Dent Corn."

With specific reference to FIG. 1, a typical corn dry-milling process 10 begins with a milling step 12 in which dried whole corn kernels are passed through hammer mills to grind them into meal or a fine powder. The ground meal is mixed with water to create a slurry, and a commercial enzyme such as alpha-amylase is added. This slurry is then typically heated in a cooking process 14, which can optionally include a jet cooker process, to solubilize the starch in the ground meal. This is followed by a liquefaction step 16 at which point additional alpha-amylase may be added. The alpha-amylase hydrolyzes the gelatinized starch into maltodextrins and oligosaccharides to produce a liquefied mash or slurry.

This can be followed by separate saccharification and fermentation steps, 18 and 20, respectively, although in most commercial dry-milling ethanol processes, saccharification and fermentation occur simultaneously. In the saccharification step 18, the liquefied mash is cooled and a commercial enzyme, such as gluco-amylase, is added to hydrolyze the maltodextrins and short-chained oligosaccharides into single glucose sugar molecules. In the fermentation step 20, a common strain of yeast (*Saccharomyces cerevisae*) is added to metabolize the glucose sugars into ethanol and $CO_2$. Upon completion, the fermentation mash ("beer") contains about 17% to 18% ethanol (volume/volume basis), plus soluble and insoluble solids from all the remaining grain components, including fiber, protein, and oil, for example. Yeast or another fermentation agent can optionally be recycled in a yeast/fermentation agent recycling step 22. In some instances, the $CO_2$ is recovered and sold as a commodity product.

Subsequent to the fermentation step 20 is a distillation and dehydration step 24 in which the beer is pumped into distillation columns where it is boiled to vaporize the ethanol. The ethanol vapor exits the top of the distillation columns at about 95% purity (190 proof) and then is condensed to a liquid ethanol in a typical heat exchanger. The 190 proof ethanol typically then goes through a molecular sieve dehydration column or the like, which removes the remaining residual water from the ethanol, to yield a final product of essentially 100% ethanol (199.5 proof; referred to herein as "200 proof").

Finally, a centrifugation step 26 involves centrifuging, via a decanter centrifuge, the residuals or whole stillage leftover from distillation so as to separate the insoluble solids portion or "wet cake", which includes fiber, germ particles, and larger solids from the liquid portion or "thin stillage" portion, which includes fine solids, soluble solids, protein, amino acids, oil, etc. Next, the thin stillage portion enters evaporators in an evaporation step 28 in order to boil away moisture thereby leaving a thick syrup, which contains the soluble (dissolved) solids as well as fine protein and oil. This concentrated syrup is typically referred to as corn condensed distillers soluble and is mixed with the centrifuged wet cake then sold to beef and dairy feedlots as distillers wet grain with solubles (DWGS). The wet cake and concentrated syrup mixture may be further dried in a drying step 30 and sold as distillers dried grain with solubles (DDGS) to dairy and beef feedlots and/or the monogastric markets. The distiller's grains with solubles co-product provides a critical secondary revenue stream that offsets a portion of the overall ethanol production cost.

Figure 2:
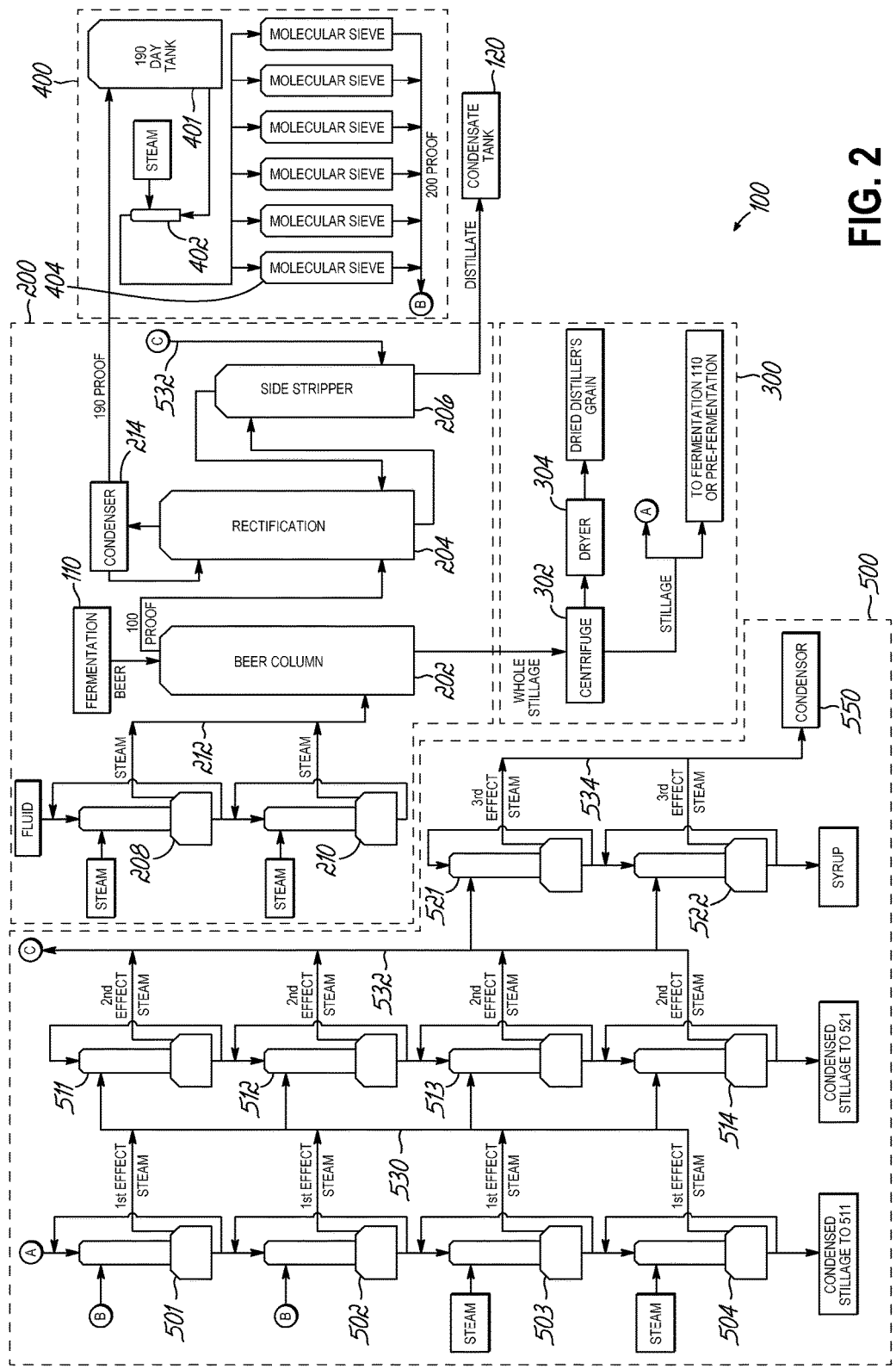
FIG. 2 is a flow diagram of a method and system for distilling alcohol in an alcohol production process in accordance with an embodiment of the invention.

In accordance with the present invention, FIG. 2 schematically illustrates an embodiment of a method and system, collectively numeral 100, for producing alcohol, e.g., ethanol, in a grain dry-milling process, such as a corn or similar grain dry-milling process. The method and system 100 can include a fermentation process 110, a distillation process 200, a separation process 300, a dehydration process 400, and an evaporation process 500.

Figure 3:
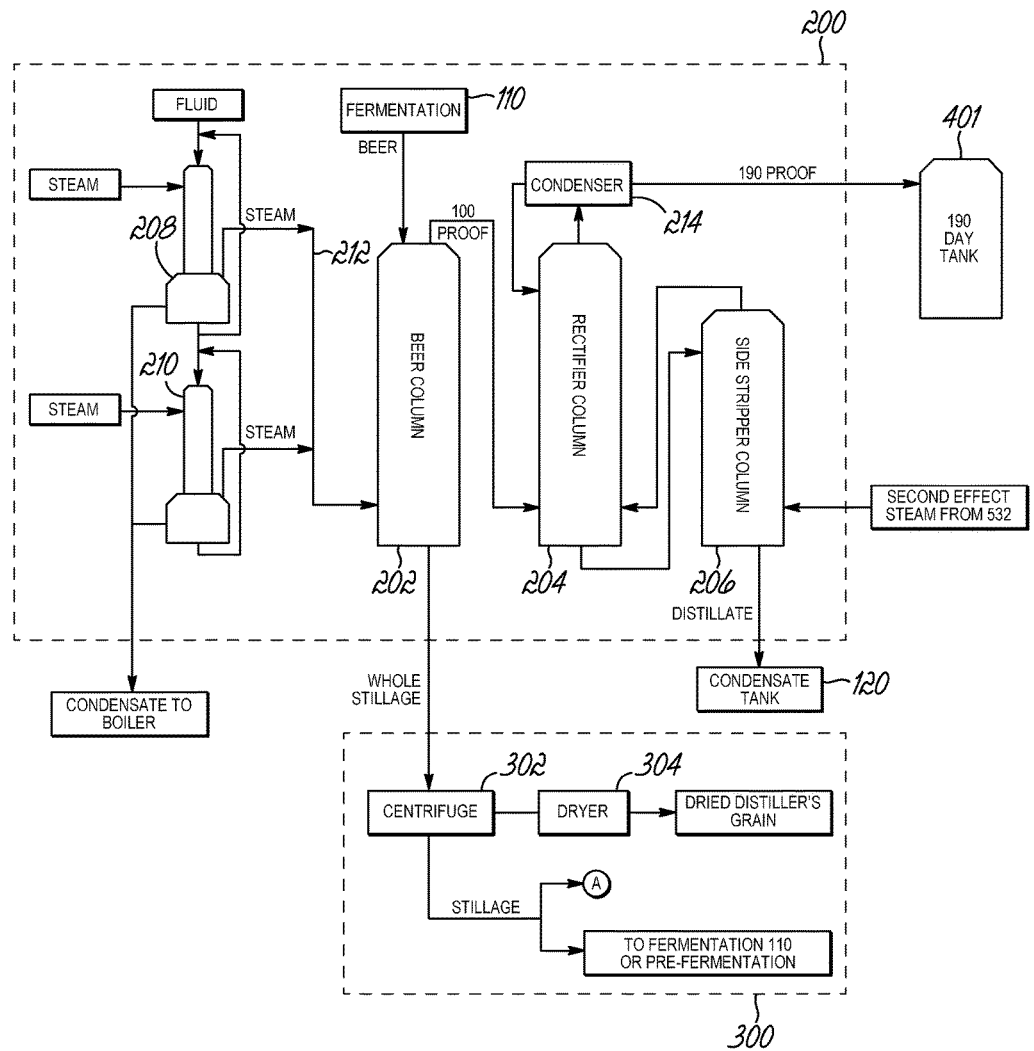
FIG. 3 is a flow diagram showing the distillation and separation processes of the method and system of FIG. 2.

As shown in FIGS. 2 and 3, the distillation process 200 can include a beer column 202, a rectifier column 204, and a side stripper column 206. Each of the beer column 202, rectifier column 204, and side stripper column 206 are multi-tray vessels and operate at subatmospheric conditions. The beer column 202 can receive ethanol laden beer from the fermentation process 110. The beer includes ethanol, water, and milled grain components and can have an ethanol concentration of approximately 17-18% (volume/volume basis). The temperature of the beer entering the beer column 202 may be about 150° F. and may be at a pressure of about 7 psia. The beer column 202 may be operated at a pressure in a range of about 4 psia to about 11 psia or about 5 psia to about 12 psia, with a corresponding temperature range of about 140° F. up to about 165° F. In one embodiment, the operating pressure may be about 7 psia. Temperatures much greater than 165° F. can cause flashing within the vessel, increasing the potential for beer or mash to carryover the top of the beer column 202 and into the rectification column 204. Higher operating temperatures can be realized due to changes in the alcohol content of the mass fed to the beer column 202. Steam from at least one set of steam generators 208 and 210 provides heat or thermal energy for boiling off the alcohol/ethanol from the beer in the beer column 202. The source and routing of this steam is described in greater detail below. The steam is mixed directly with the beer as the beer cascades down through the beer column 202. The overhead ethanol vapor leaving the beer column 202 is about 50% ethanol or 100 proof.

The steam generators 208, 210 can each include a shell and tube heat exchanger in which a heating vapor may be isolated in the shell side. The heating vapor may be clean plant steam from a plant boiler (not shown). In one example, the clean plant steam may be at a pressure of about 164 psia and a temperature of about 365° F. In another example, the clean plant steam may be at a pressure between 134 psia and 164 psia and at a temperature of between 350° F. and 365° F. The steam will condense and exit as condensate through condensate lines. The steam condensate can be returned to the boiler (not shown). The tube-side fluid entering the steam generators 208, 210 may vary and can be evaporator condensate from the evaporation process 500, which is further discussed below, distillate from condensate tank 120, cook water, or $CO_2$ scrubber water from the front end of the method and process 100, or a combination thereof. During operation, the tube-side fluid can enter the top of the steam generator 208 and remaining fluid can leave the bottom of the steam generator 208 whereat it can enter the top of subsequent steam generator 210. In one example, the fluid exiting the steam generator 208 may be split so that a portion is recycled to the top of the steam generator 208 and the remainder enters steam generator 210. Remaining fluid exiting steam generator 210 may be returned to its top or may be split so that a portion is recycled to the top of steam generator 210 and the remainder enters steam generator 208.

Tube side fluid that is boiled off or evaporated in the steam generators 208, 210, which may be referred to as first effect steam, can enter a steam line 212, which leads to the beer column 202. The range of the steam temperature is a function of the pressure, which can be in a range of about 9 psia to about 14 psia with a corresponding temperature range of about 188° F. to about 209° F. In another example, the steam may be at a pressure between 12 psia and 14 psia and at a temperature of between 202° F. and 209° F. The various lines leading to and from the steam generators 208, 210 may be valved so that any one of the steam generators 208, 210 can be selectively taken off-line and by-passed for maintenance. As such, the ethanol facility can be designed to operate at full capacity with a single steam generator 208, 210 on-line. Thus, any one of the steam generators 208, 210 can be isolated and shut down for cleaning and maintenance without compromising the operation of the plant. Although there are two steam generators 208, 210 shown in FIG. 2, it should be understood that only one or more than 2 may be provided, as desired/needed. The total number of steam generators (or sets of steam generators) can be driven by the production volume requirements of the plant. Additionally, a thermo compressor (not shown) can be utilized on the steam feeding the steam generators 208, 210 to improve, for example, the thermal efficiency of the steam generators 208, 210.

With further reference to FIGS. 2 and 3, the 100 proof ethanol vapor from the beer column 202 enters the rectifier column 204 where ethanol vapor having a higher concentration of ethanol (190 proof or 95% pure) is generated as an overhead vapor at a pressure of about 4 psia. Accordingly, the operating pressure of the rectifier column 204 may be about 4 psia. The rectifier column 204 can be operated at a subatmospheric pressure in a range of about 2.5 psia to about 6.0 psia. Other operating ranges are contemplated here. Vapor flowing out of the rectifier column 204 is condensed into a liquid by a condenser 214. The condenser 214 may use cooling water as the condensing medium. The overhead condensed ethanol may be split so that a portion (e.g., two-thirds) is recycled back into the rectifier column 204 and the remainder (e.g., one-third) is sent to a 190 day tank 401 for further processing. The thermal energy or heat that drives the rectifier column 204 is present in the hot 100 proof vapors that enter the rectifier column 204. The bottoms from the rectifier column 204, which have an ethanol concentration of about 20% (or 40 proof), are circulated to the side stripper column 206.

Figure 5:
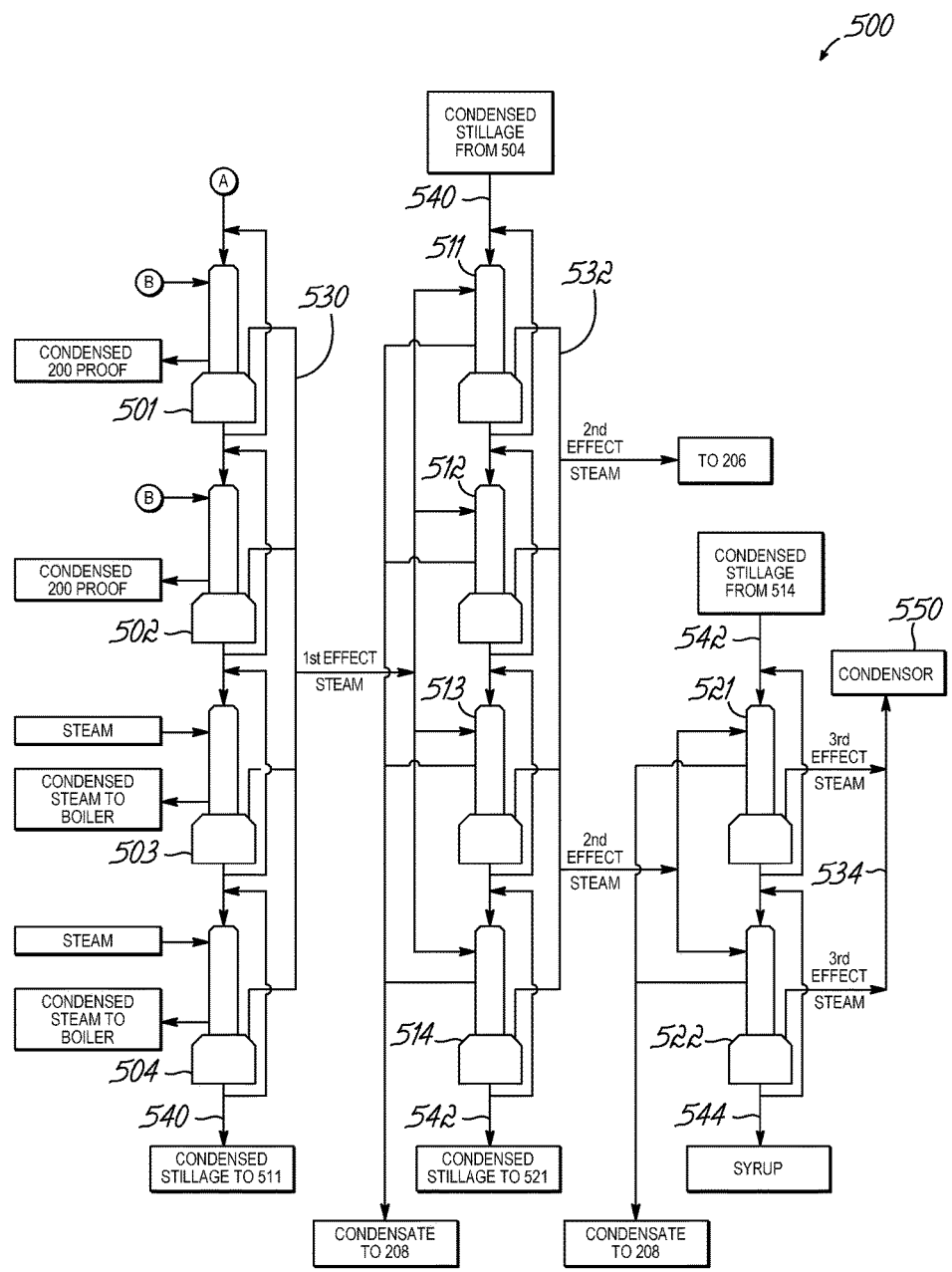
FIG. 5 is a flow diagram showing the evaporation process of the method and system of FIG. 2.

The side stripper column 206 strips ethanol from the rectification bottom stream and produces a second stream of 80 proof vapor that is circulated back into the rectifier column 204 for further dehydration or separation of the ethanol from the distillate stream. The ethanol proof of the vapor circulated back to the rectifier column 204 can have a range of about 60 to about 120. The side stripper column 206 may operate at a pressure of about 7 psia. The side stripper column 206 can be operated at a pressure in a range of about 5 psia to about 9 psia. Other operating ranges are contemplated here. The side stripper column 206 can be heated by the thermal energy of second effect steam from a second set of evaporators 511, 512, 513, 514 (FIG. 5). The source and routing of this second effect steam is described in greater detail below. The bottoms or distillate from the side stripper column 206 is mostly hot water, which can be sent to a condensate tank 120 and/or optionally used in initially slurrying the ground grain.

With continuing reference to FIGS. 2 and 3, the separation process 300 receives beer bottoms or whole stillage containing mostly water, dissolved materials, unfermented solids and spent fermentation from the milled grain and subsequent fermentation process 110. The separation process 300 receives the whole stillage and removes the solids known as distiller's grains. In particular, the whole stillage form the beer column 202 can be piped to a centrifuge 302 or other separation device, which separates the whole stillage into solids known as distiller's grains and a liquid referred to as stillage (or centrate). The distiller's grains can be conveyed to a dryer 304 for further drying. Because distiller's grains can be rich in fiber and protein, they can be used as a feed for livestock. The liquid portion or stillage leaving the centrifuge 302 may be sent on or divided, for example, into two portions, as follows. All or a portion of the resulting stillage can be piped to the evaporation process 500 of the system, which is further discussed in more detail below. A second optional portion can be piped to fermentation 110 and/or pre-fermentation, such as to create a slurry with the ground grain. A third optional portion can be further utilized or processed into an additional component as follows, including but not limited to use in anaerobic digestion, as a nutrient feed source for a biochemical or biofuel fermentation or conversion process, as feed for an herbicide or a fertilizer, utilized as a feed source for zein protein or any other viable usage.

Figure 4:
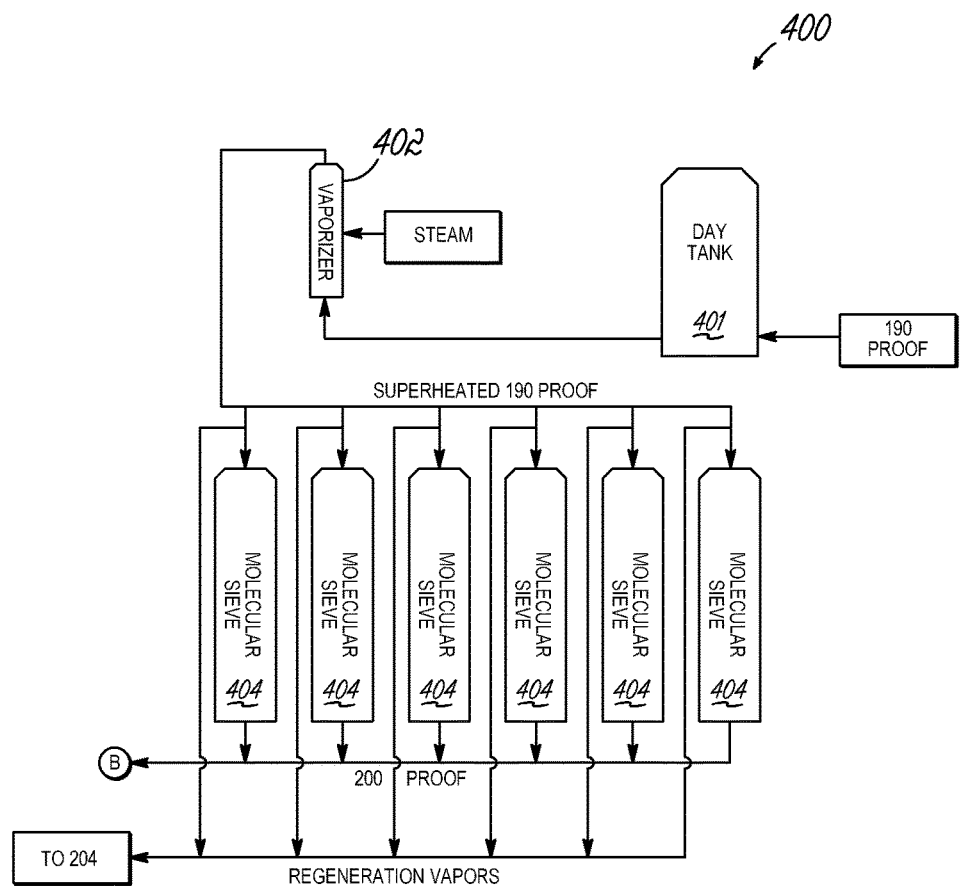
FIG. 4 is a flow diagram showing the dehydration process of the method and system of FIG. 2.

With reference now to FIGS. 2 and 4, the dehydration process 400 receives liquid 190 proof hydrous ethanol from the condenser 214 in the distillation process 200 and removes most of the remaining water in that ethanol. In the dehydration process 400, the liquid 190 proof (hydrous)

ethanol from the 190 day tank 401 is vaporized via a steam vaporizer 402 to ensure no no condensing of the hydrous ethanol occurs in the molecular sieves 404. To that end, the superheated 190 proof ethanol is sent to a series of molecular sieves 404 where excess water is removed to produce about a 97.0% (or greater) by weight ethanol stream commonly referred to as anhydrous ethanol or 200 proof ethanol. In one example, about a 99.0% (or greater) by weight ethanol stream is produced. The molecular sieves 404 can be multi-column systems containing vessels, vaporizers, regeneration condensers, and reclaim heat exchangers. In one example, each of the molecular sieves 404 include a packed column of desiccant beads that attract water but reject ethanol to remove the water from the hydrous ethanol. The resulting hot 200 proof ethanol vapor leaving the molecular sieve 404 is sent to the evaporation process 500, as further discussed below. Once the desiccant beads are saturated with water, they can be regenerated by pulling a high vacuum, which can be accomplished by taking them offline. The high vacuum flashes the water and any ethanol from the desiccant beads, and the beads are ready to be placed in service again. The vapors released in this regeneration cycle are sent back to the rectifier column 204 to be captured. It should be understood that the molecular sieves 404 may be replaced with other types of dehydration devices, e.g., steel or ceramic membranes, pervapor separation, or chemical separation, all of which can perform the desired dehydration function.

With reference now to FIGS. 2 and 5, three sets of evaporators can be utilized in the evaporation process 500, in part, to reduce or concentrate the stillage from the separation process 300 to a thick syrup, which can be fed to the dryer 304 for further drying. The stillage may contain approximately 2 to 8% solids, with a range of about 4 to 10%, at the beginning of the evaporation process 500, and the resulting syrup may have a solids concentration of 34 to 36%, with a range of about 25 to 50% solids concentration. The three sets of evaporators, which together provide a triple effect evaporation process, can include a first set of evaporators 501, 502, 503, 504, known as first effect evaporators, a second set of evaporators 511, 512, 513, 514, known as second effect evaporators, and a third set of evaporators 521, 522, known as third effect evaporators. Although each set of first and second effect evaporators is illustrated as having four evaporators, each set could include less than four, e.g., one, two, or three, or more than four evaporators, as needed. Similarly, although the third effect evaporators are illustrated as having only two evaporators, this effect may include less than or more than two, e.g., 1, 3, 4, etc, as needed. With this setup, energy for the side stripper column 206 can be created from the evaporation of water from the stillage, as discussed next.

Each of the evaporators in the evaporation process 500 can include a shell and tube heat exchanger in which a heating vapor is isolated in the shell side. The set of first effect evaporators are heated by a heating vapor such as clean plant steam from a boiler (not shown) or hot 200 proof ethanol vapor from the molecular sieves 404. In an embodiment, the heating vapor for the evaporator 501, 502 is the hot 200 proof ethanol vapor, while the heating vapor for the evaporators 503, 504 is steam from the plant boiler (not shown). It should be understood here that various modifications may be made altering which of the first effect evaporators 501, 502, 503, 504 are provided with steam and/or the hot 200 proof ethanol vapor. In one example, the clean plant steam may be at a pressure of about 24 psia and a temperature of about 242° F. In another example, the temperature may be in a range of about 240° F. to 245° F. In another example, the clean plant steam may be at a pressure between 14 psia and 23 psia and at a temperature from 210° F. to 235° F. And in one example, the hot 200 proof ethanol vapor may be at a pressure of about 50 psia and a temperature of about 280° F. In still another example, the hot 200 proof ethanol vapor may be at a pressure in a range of about 30 psia and about 65 psia and at a temperature from about 250° F. to about 320° F. In one example, the hot 200 proof ethanol vapor is not mixed with plant steam. The heating vapor from the incoming steam or hot 200 proof ethanol vapor will condense and exit as liquid ethanol or steam condensate through condensate drain lines. The steam condensate can be returned to the boiler (not shown), for example, and/or sent to steam generator 208 and/or 210 for use as all or a part of the tube side fluid. The condensed 200 proof ethanol liquid can be sent through a single exchanger or a series of exchangers (not shown) to exchange additional heat into the 190 proof ethanol liquid feed to the dehydration step (400). The cooled 200 proof ethanol, which is the main final product of the ethanol facility, is then sent to a 200 proof tank (not shown). The cooled 200 proof ethanol liquid can optionally be added to the 200 proof vapor (desuperheat) feeding the evaporator 501 and/or 502 to improve the overall heat transfer and vapor condensing capacity in order to reclaim the heat of condensing within the evaporator chest.

With continuing reference to FIGS. 2 and 5, the stillage from the separation process 300 can be sent to the evaporators 501, 502, 503, 504. An optional portion of the stillage can be sent to the front end of the method and system 100, such as to help create a slurry with the ground grain. In this embodiment, the stillage from centrifuge 410 can enter the top of the evaporator 501, leave the bottom of evaporator 501 slightly concentrated, and enters the top of the next evaporator 502. It should be understood here that various modifications may be made altering which of the first effect evaporators 501, 502, 503, 504 are initially provided with stillage. The stillage exiting the evaporator 501 may be split so that a portion is recycled to the top of the evaporator 501 and the remainder enters the next evaporator 502. Similarly, a portion of the stillage may be recycled from the bottom of the evaporators 502, 503, and/or 504 to their tops. The concentrated stillage finally exits the bottom of evaporator 504 via stillage line 540. The concentrated stillage may be referred to as first-concentrated stillage after it leaves the first set of evaporators. Liquid that is boiled off or evaporated from the stillage in the evaporators 501, 502, 503, 504 can enter a first effect steam line 530 as steam. Because evaporators 501, 502, 503, 504 produce first effect steam that is used to heat the evaporators 511, 512, 513, 514, they are known as first effect evaporators. The various lines leading to and/or leaving the evaporators may be valved so that any one of the four evaporators 501, 502, 503, 504 can be selectively taken off-line and by-passed for maintenance. The ethanol facility can be designed to operate at full capacity with three (or less) first effect evaporators on-line. Thus, any one of the four evaporators can be isolated and shut down for cleaning and maintenance without compromising the operation of the plant. Depending on the facility production rate, it is known by one skilled in the art that the number of first effect evaporators can vary from 1 to more than 4. The total number of evaporators typically is driven by the production volume requirements.

With continuing reference to FIGS. 2 and 5, the arrangement and operation of the second effect evaporators 511, 512, 513, 514 is somewhat similar to the first effect evaporators 501, 502, 503, 504 except, for example, that they operate at a lower pressure and temperature and are heated by first effect steam collected from first effect evaporators 501, 502, 503, 504. The first effect steam generated by the first effect evaporators is preferably at a pressure of about 14 psia to about 17 psia and at a temperature of about 210° F. to about 225° F. The second effect evaporators process the concentrated stillage from the stillage line 540. Specifically, the concentrated stillage from the stillage line 540 enters evaporator 511, which further concentrates the stillage. The stillage exiting the evaporator 511 may be split so that a portion is recycled to the top of the evaporator 511 and the remainder enters the next evaporator 512. In this manner, the stillage is concentrated by each of the evaporators 511, 512, 513, 514. The concentrated stillage finally exits the evaporator 514 via stillage line 542. The steam generated in the second effect evaporators 511, 512, 513, 514 is second effect steam. This relatively low pressure, second effect steam is collected from the various outlets of second effect evaporators 511, 512, 513, 514 by second effect steam line 532. The second effect steam line 532 then conveys a portion of the second effect steam to the side stripper column 206 (e.g., one-third) and the remainder to the third effect evaporators 521, 522 (e.g., two-thirds). The further concentrated stillage may be referred to as second-concentrated stillage after it leaves the second set of evaporators.

The second effect steam that is conveyed to the side stripper column 206 is preferably at a pressure of about 10.5 psia to about 11.5 psia and at a temperature of about 195° F. to about 200° F. Because the evaporators 511, 512, 513, 514 produce second effect steam that is used to heat the evaporators 521, 522, they are known as second effect evaporators. The first effect steam is condensed and a portion of the condensate can be sent to the front end of the method and system 100, such as to help create a slurry with the ground grain, for example, and/or sent to steam generator 208 and/or 210 for use as all or a part of the tube side fluid. As with the first effect evaporators, the various lines leading to and/or from the evaporators may be valved so that any one of the four evaporators 511, 512, 513, 514 can be selectively taken off-line and by-passed for maintenance allowing for continuous operation. And depending on the facility production rate, it is known by one skilled in the art that the number of second effect evaporators can vary from 1 to more than 4. The total number of evaporators typically is driven by the production volume requirements.

With further reference to FIG. 5, the arrangement and operation of the third effect evaporators 521, 522 is somewhat similar to the second effect evaporators 511, 512, 513, 514 except, for example, that they operate at a lower pressure and temperature and are heated by at least a portion of the second effect steam collected from the second effect evaporators 511, 512, 513, 514. The second effect steam generated by the second effect evaporators that is used to heat the third effect evaporators 521 and/or 522 is preferably at a pressure of about 10.5 psia to about 11.5 psia and at a temperature of about 195° F. to about 200° F. The evaporators 521, 522 further process the concentrated stillage from the stillage line 542. Specifically, the concentrated stillage from the stillage line 542 enters the evaporator 521, which further concentrates the stillage.

The stillage exiting the evaporator 521 may be split so that a portion is recycled to the top of the evaporator 521 and the remainder enters the next evaporator 522. In this manner, the stillage is concentrated by each of the evaporators 521, 522. The concentrated stillage finally exits the evaporator 522 as a syrup that is conveyed via syrup line 544 back to, for example, a syrup storage tank (not shown) and/or the dryer 304. The relatively low pressure, steam is collected from the various outlets of evaporators 521, 522 by a steam line 534. The third effect steam generated in the evaporators 521, 522 is sent to a condenser 550. It should be understood that the condenser 550 may be replaced with other types of heat recovery devices, and the heat recovered from the steam may be used in other portions of the method and system 100. For example, heat recovered from the third effect steam from the evaporators 521, 522 may be used to heat the beer feed entering the beer column 202, the slurry tank, the boiler feed water, etc. The second effect steam is condensed and a portion of the condensate can be sent to the front end of the method and system 100, such as to help create a slurry with the ground grain, and/or sent to steam generator 208 and/or 210 for use as all or a part of the tube side fluid. As with the first and second effect evaporators, the various lines leading to and/or from the third effect evaporators 521, 522 may be valved so that any one of the evaporators 521, 522 can be selectively taken off-line and by-passed for maintenance allowing for continuous operation. And depending on the facility production rate, it is known by one skilled in the art that the number of third effect evaporators can vary from 1 to more than 2. The total number of evaporators typically is driven by the production volume requirements.

It should be recognized that the order of the evaporators through which the stillage passes may vary. As described above, the stillage passes through the evaporators 501, 502, 503, 504, 511, 512, 513, 514, 521, 522, in order. In another embodiment, the stillage may pass through the evaporators 501, 502, 503, 511, 512, 513, 514, 521, 522, 504, in order. Other modifications and variations are contemplated. Modifying the order of the evaporators through which the stillage passes does not affect the order or configuration of the first and second effect steam flows.

With reference again to FIGS. 2 and 3, inside the side stripper column 206, ethanol present in the bottoms produced by the rectifier column 204 is boiled out as overhead 80 proof vapor. The second effect steam from the second effect evaporators 511, 512, 513, 514 provides the necessary steam to remove the remaining ethanol from the bottoms. The quantity of second effect steam needed from evaporators 511, 512, 513, 514 for efficient ethanol recovery determines the evaporation capacity of the evaporation process 500. The steam requirements of the side stripper column 206 of the distillation process 200 helps determine the evaporation capacity of the evaporation process 500. When the steam requirement of the side stripper column 206 increases, the evaporation capacity of the evaporation process 500 increases, so that more stillage from the separation process 300 can be conveyed to the evaporation process 500 and less stillage sent elsewhere, such as to fermentation 110 or pre-fermentation, as discussed above. Conversely, when the side stripper column 206 requires less steam, then less stillage is sent to the evaporation process 500 and more can be used elsewhere. On average, approximately 50% of the stillage from the separation process 300 is sent to the evaporation process 500, with a range of about 40 to about 60% as typical. This range can be more broadly extended due to the integration of the condensate evap as part of the overall energy and distillation system, and other ranges can be utilized depending upon other processing systems and conditions.

The use of second effect steam generated by the evaporators 511, 512, 513, 514 to heat the side stripper column 206 of the distillation process 200 provides important advantages. Although a vacuum must be maintained in the side stripper column 206 and the other distillation columns, the low temperature operation is not only adequate for boiling off ethanol, it is advantageous. Lower temperature operation greatly reduces the deposition of solids within the side stripper column 206. Further, the use of second effect steam eliminates the need to use clean plant steam in a distillation process, which is more thermo-efficient than the current art. In the distillation and evaporation processes 200, 500, clean plant steam is only used in shell and tube heat exchanger portions of the first effect evaporators and the vapor generators 208, 210 and where it can be isolated from contaminants so that it can be easily reused in steam boilers as make up water.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the scope of applicant's general inventive concept.

What is claimed is:

1. A method for distilling alcohol in an alcohol production process, the method comprising:
   fermenting a mixture of water and milled grain to produce alcohol-laden beer;
   distilling the alcohol-laden beer in a beer column maintained at a subatmospheric pressure to produce a vapor, primarily including alcohol, and whole stillage, which includes stillage;
   evaporating water from all or a portion of the stillage via one or more evaporators;
   generating steam from a fluid via one or more steam generators, which do not receive the stillage; and
   using at least a portion of the generated steam from the one or more steam generators to supply sufficient heat to the beer column for distilling the alcohol-laden beer to produce alcohol.

2. The method of claim 1 further comprising:
   concentrating the vapor, primarily including alcohol, in a rectifier column to produce a concentrated vapor, primarily including alcohol, and a bottoms portion;
   removing alcohol from the bottoms portion in a side stripper to produce a vapor, primarily including alcohol, and a distillate; and
   wherein evaporating water from all or a portion of the stillage via one or more evaporators comprises:
   evaporating water from all or a portion of the stillage via the one or more evaporators to produce first-concentrated stillage and first effect steam;
   evaporating water from the first-concentrated stillage via one or more additional evaporators with heat from the first effect steam to produce second-concentrated stillage and second effect steam; and
   using at least a portion of the second effect steam to supply sufficient heat to the side stripper to remove the alcohol from the bottoms portion.

3. The method of claim 2 further comprising evaporating water from the second-concentrated stillage via one or more additional evaporators with heat from the second effect steam to produce a syrup.

4. The method of claim 2 further comprising:
   condensing the concentrated vapor, primarily including alcohol, into a liquid primarily including alcohol;
   dehydrating a vaporized form of the liquid, primarily including alcohol, to produce a vapor including about 97.0% or greater alcohol; and
   using the vapor including about 97.0% or greater alcohol to supply sufficient heat to the one or more evaporators to evaporate water from the stillage to produce at least a portion of the first effect steam.

5. The method of claim 2 further comprising using steam to supply sufficient heat to the one or more evaporators to evaporate water from the stillage to produce at least a portion of the first effect steam.

6. The method of claim 1 wherein the one or more steam generators include two or more steam generators.

7. The method of claim 6 wherein the two or more steam generators are arranged together in a series fashion.

8. The method of claim 1 further comprising recycling at least a portion of the fluid from the one or more steam generators after steam generation and subjecting the recycled portion to steam generation again via the one or more steam generators to produce steam.

9. The method of claim 1 further comprising using steam to supply sufficient heat to the one or more steam generators to generate the steam from the fluid to supply sufficient heat to the beer column for distilling the alcohol-laden beer to produce alcohol.

10. The method of claim 1 wherein the generated steam is at about 9 psia to about 14 psia.

11. The method of claim 1 wherein the generated steam is at a temperature of about 188° F. to 209° F.

12. The method of claim 1 wherein the fluid for the one or more steam generators includes evaporator condensate from evaporation of the stillage, distillate from a side stripper, cook water, or carbon dioxide scrubber water, or a combination thereof.

13. The method of claim 1 wherein generating steam from a fluid via one or more steam generators, which do not receive the stillage, comprises generating steam from the fluid via two steam generators, which do not receive the stillage, by using steam to supply sufficient heat to the two steam generators to generate the steam from the fluid to supply sufficient heat to the beer column for distilling the alcohol-laden beer to produce alcohol.

14. The method of claim 1 wherein the alcohol is ethanol.

15. The method of claim 2 further comprising:
   condensing the concentrated vapor, primarily including alcohol, into a liquid primarily including alcohol;
   dehydrating a vaporized form of the liquid, primarily including alcohol, to produce a vapor including about 97.0% or greater alcohol; and
   using steam and the vapor including about 97.0% or greater alcohol to supply sufficient heat to the one or more evaporators to evaporate water from the stillage to produce the first effect steam.

16. A system for distilling alcohol in an alcohol production process, the system comprising:
   a beer column that receives alcohol-laden beer, the beer column distills the alcohol-laden beer at a subatmospheric pressure to produce a vapor, primarily including alcohol, and whole stillage, which includes stillage;
   a first effect evaporator system that includes one or more evaporators that receive all or a portion of the stillage, the one or more evaporators configured to evaporate water from the stillage; and
   one or more steam generators that receive a fluid and are configured to generate steam from the fluid, the one or more steam generators do not receive the stillage, wherein the beer column receives at least a portion of the generated steam from the one or more steam generators, whereby the steam provides sufficient heat for distilling the alcohol-laden beer in the beer column to produce alcohol.

17. The system of claim 16 wherein the one or more evaporators are configured to evaporate water from the stillage to produce first-concentrated stillage and first effect steam, the system further comprising:
a rectifier column that receives the vapor from the beer column and that concentrates the vapor to produce a concentrated vapor, primarily including alcohol, and a bottoms portion;
a side stripper that receives the bottoms portion from the rectifier and that produces a vapor, primarily included alcohol, and a distillate; and
a second effect evaporator system that is situated after the first effect evaporator system and includes one or more evaporators, which receive the first-concentrated stillage and evaporate water from the first-concentrated stillage with heat from the first effect steam to produce second-concentrated stillage and second effect steam,
wherein the side stripper receives at least a portion of the second effect steam to supply sufficient heat to the side stripper to remove the alcohol from the bottoms portion.

18. The system of claim 17 further comprising:
a third effect evaporator system that is situated after the second effect evaporation system and that includes one or more evaporators, which receive the second-concentrated stillage and evaporate water from the second-concentrated stillage with heat from the second effect steam to produce a syrup.

19. The system of claim 17 further comprising:
a condenser that receives the concentrated vapor, primarily including alcohol, from the rectifier, and condenses the concentrated vapor into a liquid primarily including alcohol; and
a dehydrating apparatus that receives a vaporized form of the liquid and dehydrates the vaporized form to produce a vapor including about 99.0% or greater ethanol,
wherein one or more evaporators of the first effect evaporator system receive the vapor including about 99.0% or greater alcohol to supply sufficient heat to the one or more evaporators to evaporate water from the stillage to produce at least a portion of the first effect steam.

20. The system of claim 16 further comprising a steam apparatus that is configured to generate steam and supply sufficient heat, via the generated steam, to one or more evaporators of the first effect evaporator system to evaporate water from the stillage to produce at least a portion of the first effect steam.

21. The system of claim 16 wherein the one or more steam generators include two or more steam generators that receive the fluid and are configured to generate steam from the fluid, the two or more steam generators do not receive the stillage.

22. The system of claim 21 wherein the two or more steam generators are arranged together in a series fashion.

23. The system of claim 16 wherein the one or more steam generators are configured to recycle at least a portion of the fluid after steam generation that is subjected to steam generation again via the one or more steam generators to produce steam.

24. The system of claim 16 further comprising a steam apparatus that is configured to generate steam and supply sufficient heat, via the generated steam, to the one or more steam generators to generate the steam from the fluid to supply sufficient heat to the beer column for distilling the alcohol-laden beer to produce alcohol.

25. The system of claim 16 wherein the generated steam is at about 9 psia to about 14 psia.

26. The system of claim 16 wherein the generated steam is at a temperature of about 188° F. to 209° F.

27. The system of claim 16 wherein the fluid for the one or more steam generators includes evaporator condensate from evaporation of the stillage, distillate from a side stripper, cook water, or carbon dioxide scrubber water, or a combination thereof.

28. The system of claim 16 wherein the one or more steam generators include two or more steam generators that receive the fluid and are configured to generate steam from the fluid, the two or more steam generators do not receive the stillage, the system further comprising:
a steam apparatus that is configured to generate steam and supply sufficient heat, via the generated steam, to the two or more steam generators to generate the steam from the fluid to supply sufficient heat to the beer column for distilling the alcohol-laden beer to produce alcohol.

29. The system of claim 16 wherein the alcohol is ethanol.

* * * * *